United States Patent [19]

DeVenuto

[11] Patent Number: 5,571,112
[45] Date of Patent: *Nov. 5, 1996

[54] METHOD AND APPARATUS FOR INSERTING AN INTRAOCULAR LENS

[75] Inventor: Joseph DeVenuto, 2955 Sugan Rd., Sulbury, Pa. 18963

[73] Assignee: Joseph DeVenuto, Sulbury, Pa.

[*] Notice: The term of this patent shall not extend beyond the expiration date of Pat. No. 5,456,487.

[21] Appl. No.: 272,195

[22] Filed: Jul. 8, 1994

Related U.S. Application Data

[63] Continuation-in-part of Ser. No. 230,426, Apr. 19, 1994, abandoned, which is a continuation of Ser. No. 973,996, Nov. 10, 1992, abandoned.

[51] Int. Cl.$^6$ .................................................. A61F 9/00
[52] U.S. Cl. .................................................. 606/107
[58] Field of Search .................. 606/228, 151, 606/107, 113; 623/4, 6

[56] References Cited

U.S. PATENT DOCUMENTS

| | | |
|---|---|---|
| 4,127,903 | 12/1978 | Schacher . |
| 4,134,161 | 1/1979 | Bayers . |
| 4,424,597 | 1/1984 | Schlegel . |
| 4,538,611 | 9/1985 | Kelman ............................. 606/113 |
| 4,575,373 | 3/1986 | Johnson . |
| 4,588,406 | 5/1986 | Fedorov et al. ...................... 623/6 |
| 4,619,657 | 10/1986 | Keates et al. ........................ 623/6 |
| 4,747,404 | 5/1988 | Jampel et al. ....................... 606/107 |
| 4,863,462 | 9/1989 | Fedorov et al. ...................... 623/6 |
| 4,872,876 | 10/1989 | Smith .................................. 623/6 |
| 4,888,012 | 12/1989 | Horn et al. .......................... 623/6 |
| 4,917,680 | 4/1990 | Poley ................................... 623/6 |
| 4,963,149 | 10/1990 | Anis .................................... 623/6 |
| 4,995,880 | 2/1991 | Galib ................................... 623/6 |
| 5,026,396 | 6/1991 | Darin .................................. 623/6 |
| 5,041,135 | 8/1991 | Charleux ............................. 623/6 |
| 5,152,789 | 10/1992 | Willis .................................. 623/6 |
| 5,176,686 | 1/1993 | Poley ................................... 623/4 |
| 5,190,553 | 3/1993 | Kanert et al. ....................... 623/6 |

OTHER PUBLICATIONS

Advertisement for Rhein Medical Fine Foldable Lens Insertion Forceps.

Advertisement for Rhein Medical Fine Universal II Forceps & Folding Block.

Advertisement for Rhein Medical Lindstrom Lens Insertion Forceps.

Brochure for Allergan Medical Optics Prodigy, Copyrighted 1990.

Brochure for Chiron Opthalmics Inc. Chiroflex Lens Microsert Model 32–IM001.

Katena Products, Inc. catalog, pp. 24 and 70.

*Primary Examiner*—Tamara L. Graysay
*Attorney, Agent, or Firm*—Steve Mendelsohn; William H. Murray

[57] ABSTRACT

The apparatus comprises a loop and a tail, where the loop has a large opening and a small opening. The loop is adapted to retain the lens in a folded position while the lens is grasped with a forceps and inserted into the eye through an incision in the eye. The tail is adapted to be pulled to release the lens from the loop. The lens is folded and inserted into the loop using a disk having a U-shaped protrusion at an edge of the disk, a recess on a surface of the disk, and a groove running across the recess and aligned with the protrusion. The lens is folded by forcing it into the groove and sliding the folded lens into the protrusion, over which the loop is placed. The loop and the loop are pulled off the protrusion together leaving the lens held in the folded state within the loop ready for insertion into the eye.

23 Claims, 9 Drawing Sheets

METHOD AND APPARATUS FOR INSERTING AN INTRAOCULAR LENS

CROSS-REFERENCES TO RELATED APPLICATIONS

This is a continuation-in-part of application Ser. No. 08/230,426, filed Apr. 19, 1994, now abandoned, which is a continuation of application Ser. No. 07/973,996, filed Nov. 10, 1992 now abandoned.

BACKGROUND OF THE INVENTION

1. Field of the Invention

The present invention relates to eye surgery, and, in particular, to a method and apparatus for inserting an intraocular lens into an eye.

2. Statement of Related Art

Figure 1:
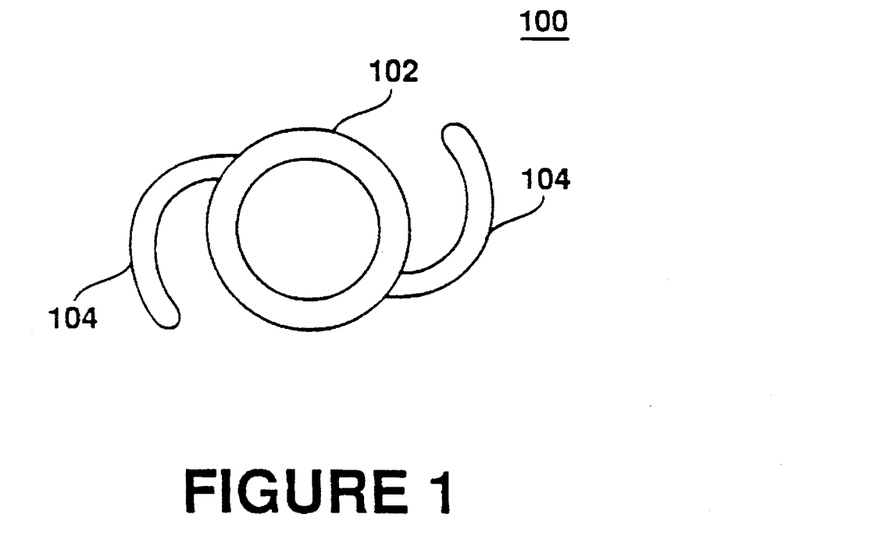
FIG. 1 shows an artificial foldable silicone intraocular lens.

When a cataract is removed from an eye, the lens may be replaced with an artificial foldable silicone intraocular lens, such as shown in FIG. 1. The lens is inserted into the eye through an incision made in the eye. In general, the smaller the incision, the better for the patient. Conventional devices for inserting the lens into the eye require incisions of at least 4.5 millimeters in length.

What is needed is a method and apparatus for inserting an intraocular lens into the eye through a small incision in the eye. A purpose of the present invention is to provide such a method and apparatus.

SUMMARY OF THE INVENTION

The present invention is an apparatus for inserting a foldable intraocular lens into an eye. According to a preferred embodiment, the apparatus comprises (a) a loop, for maintaining the lens in a folded state, the loop having a large opening and a small opening, and (b) a tail connected to the loop. The loop is adapted to retain the lens in a folded position while the lens is grasped with a forceps and inserted into the eye through an incision in the eye. The tail is adapted to be pulled to release the lens from the loop.

The present invention is also a method for inserting a foldable intraocular lens into an eye using a forceps and an apparatus having a loop and a tail. According to a preferred embodiment, the lens is grasped with the forceps, wherein the lens is held in a folded position within the loop of the apparatus, wherein the loop has a large opening and a small opening. The lens is inserted into the eye with the forceps through an incision in the eye. The tail of the apparatus is pulled to release the lens from the loop of the apparatus.

The present invention is also an apparatus for folding a foldable intraocular lens and inserting the folded lens into a loop. According to a preferred embodiment, the apparatus comprises a disk having a U-shaped protrusion positioned at an edge of the disk, a recess on a surface of the disk, and a groove running across the recess and aligned with the protrusion.

The present invention is also a method for folding a foldable intraocular lens and inserting the folded lens into a loop. According to a preferred embodiment, the lens is placed on a disk having a U-shaped protrusion at an edge of the disk, a recess on a surface of the disk, and a groove running across the recess and aligned with the protrusion. The loop is placed over the protrusion and the lens is folded by forcing the lens into the groove. The folded lens is slid along the groove into the protrusion and the loop is slipped off the protrusion and onto the folded lens.

DETAILED DESCRIPTION OF THE INVENTION

Referring now to FIG. 1, there is shown artificial foldable silicone intraocular lens 100 comprising optic 102 and haptics 104. Lens 100 is typically 6 millimeters in diameter when not in a folded state.

Figure 2:
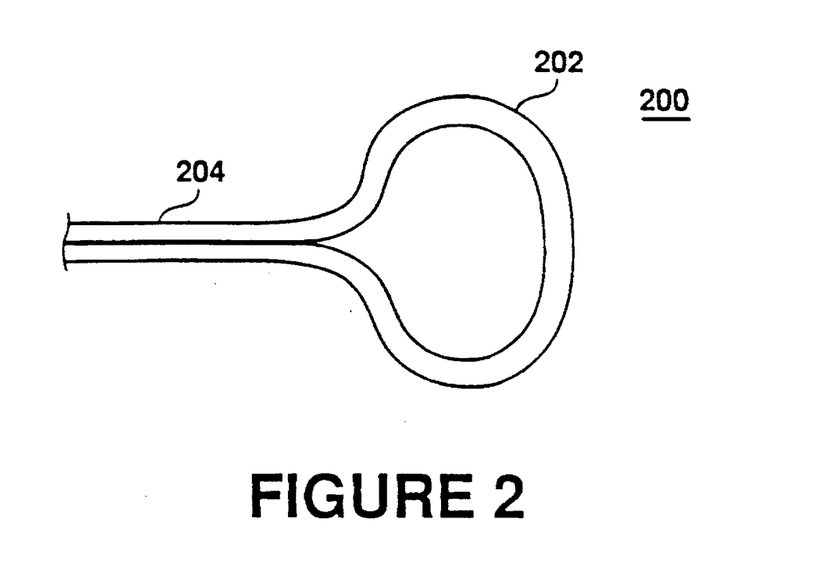
FIG. 2 shows a side view of an apparatus for inserting the lens of FIG. 1 into an eye, according to a preferred embodiment of the present invention.

Referring now to FIG. 2 there is shown apparatus 200 according the present invention for inserting lens 100 into an eye. Apparatus 200 comprises loop 202 and tail 204. Apparatus 200 may be formed by partially folding a ribbon of flexible plastic material in half lengthwise. The two ends of the ribbon are held together to form tail 204 either by heating the plastic while pressing the ends together or using an adhesive. Loop 202 is formed by only partially folding the ribbon, that is, by not forming a severe crease in the ribbon. In a preferred embodiment of the present invention, loop 202 has an inner diameter of approximately 2.7 to 2.8 millimeters and tail 204 is at least 40 millimeters long. The ribbon material from which apparatus 200 is constructed is preferably approximately 0.5 millimeters thick and 2.5 millimeters wide. Apparatus 200 may be constructed of a sterilizable plastic.

Figure 3:
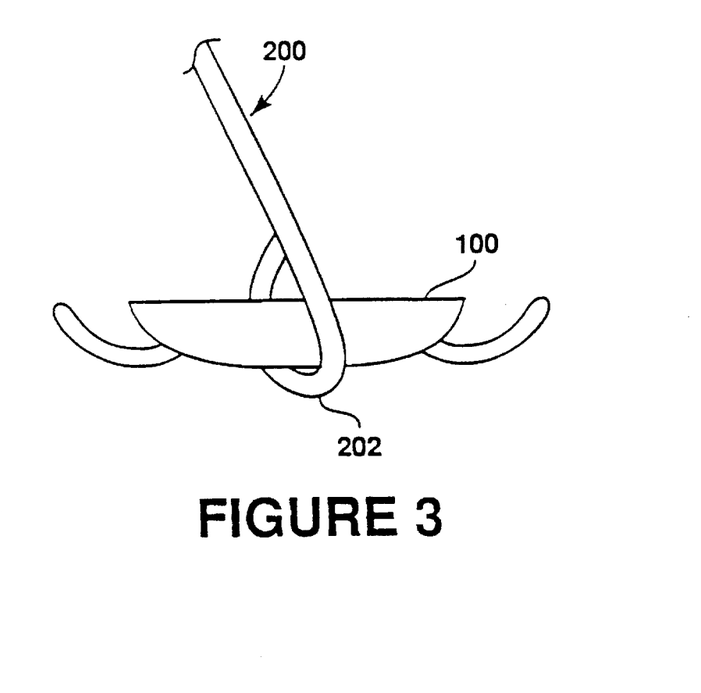
FIG. 3 shows the lens of FIG. 1 held in a folded state in the loop of the apparatus of FIG. 2.
Figure 4:
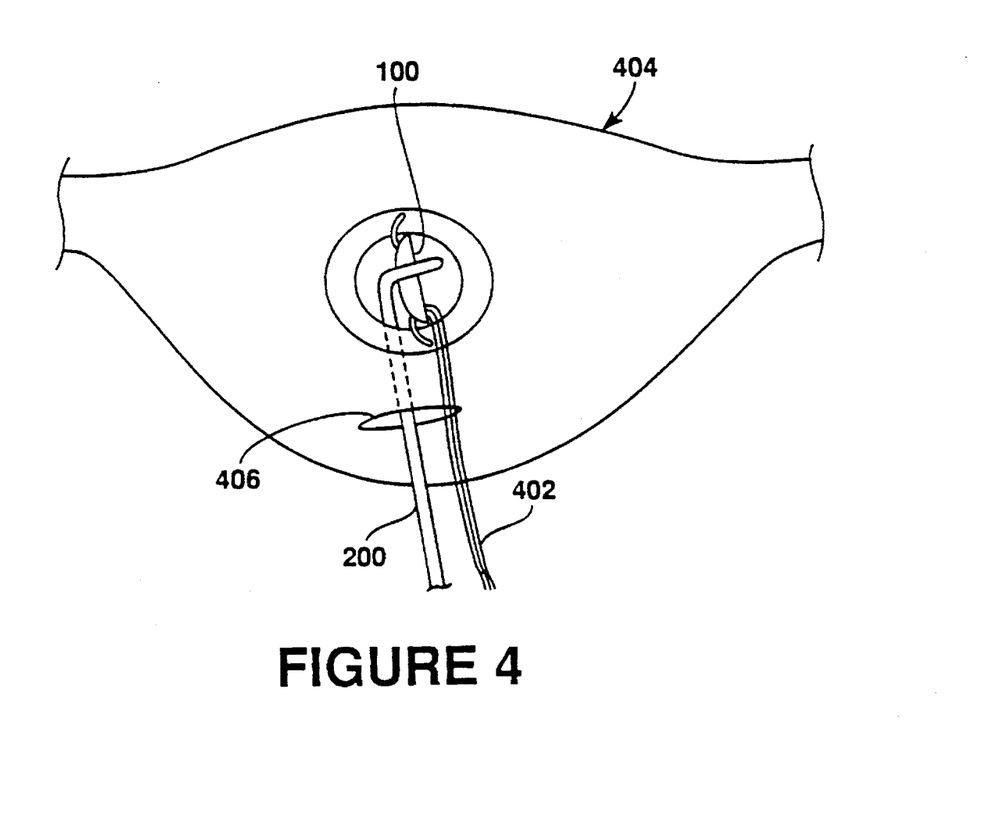
FIG. 4 shows the lens of FIG. 3 being inserted into an eye with a forceps.

Referring now to FIG. 3, there is shown lens 100 held in a folded state in loop 202 of apparatus 200. As shown in FIG. 4, folded lens 100 may be grasped with forceps 402 and inserted into eye 404 through incision 406, while lens 100 is held within loop 202 of apparatus 200. Incision 406 is preferably at most 3.5 millimeters in length. After lens 100 is properly positioned within eye 404, tail 204 of apparatus 200 may be pulled to release lens 100 from loop 202. Lens 100 is then free to unfold within eye 404. As tail 204 is pulled, loop 202 passes over the end of forceps 402. Lens 100 may then be released from forceps 402, which is removed from eye 404 along with apparatus 200 through incision 406.

Figure 5:
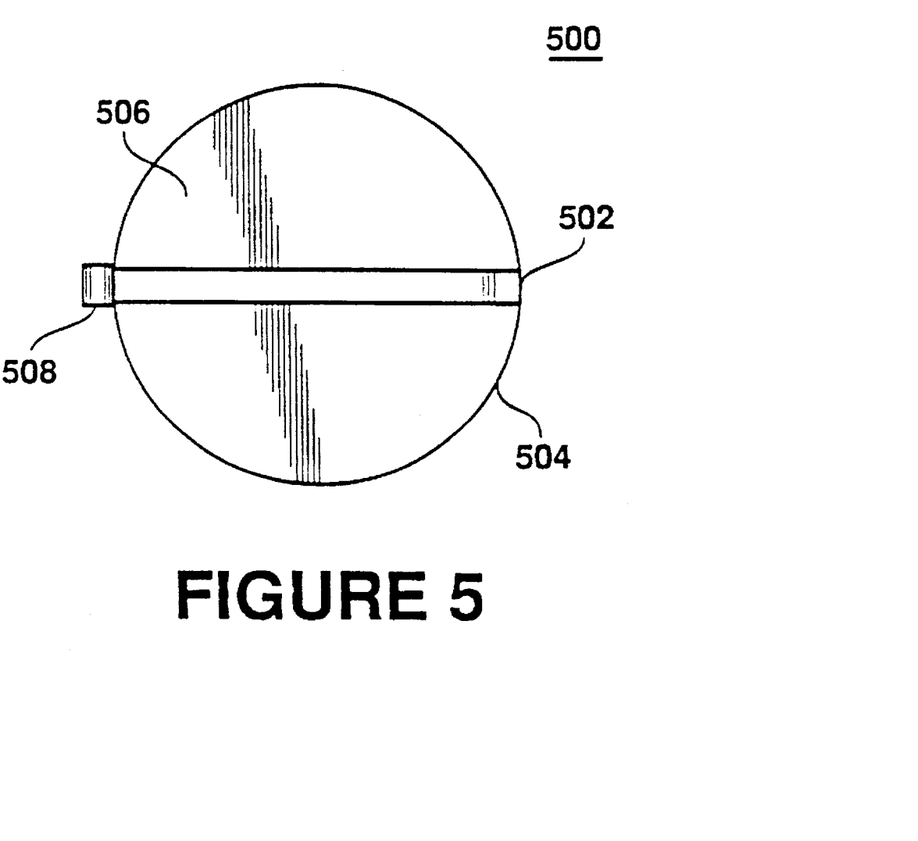
FIGS. 5, 6, and 7 show plan, side, and perspective views of an apparatus for folding the lens of FIG. 1 and inserting the folded lens into the loop of the apparatus of FIG. 2, according to a preferred embodiment of the present invention.
Figure 6:
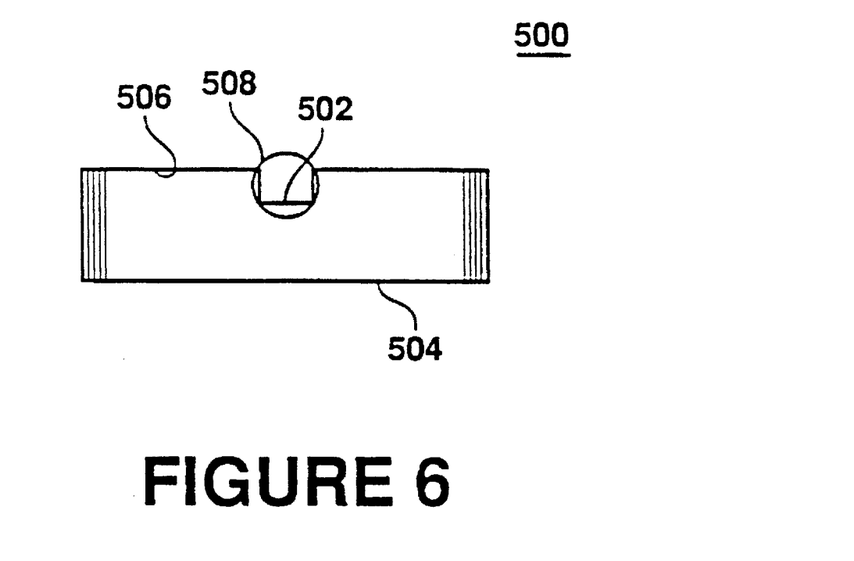
Figure 7:
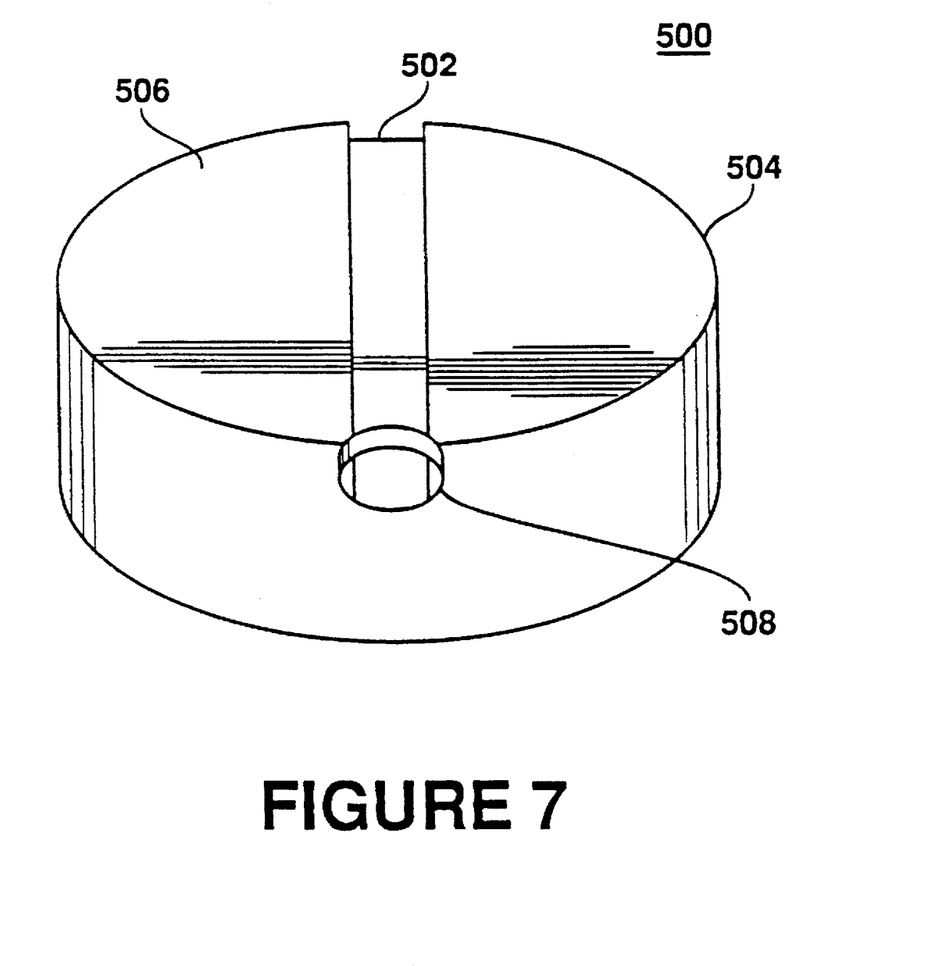

Referring now to FIGS. 5, 6, and 7, there are shown plan, side, and perspective views of apparatus 500 according to the present invention for folding lens 100 and inserting folded lens 100 into loop 202 of apparatus 200. Apparatus 500 comprises disk 504 having groove 502 along surface 506 of disk 504 and hollow protrusion 508 extending from groove 502. Disk 504 may be made of any sterilizable material and is preferably made of a hard smooth plastic that will not damage lens 100. Groove 502 is preferably approximately 2 millimeters wide, 2.8 millimeters deep, and at least 6 or 7 millimeters long. In a preferred embodiment, protrusion 508 has an outer diameter of approximately 2.5 millimeters, which is slightly smaller than the inner diameter of loop 202. Protrusion 508 is preferably about 2.5 millimeters long or roughly equivalent to the width of loop 202. The edges and corners of apparatus 500 are preferably rounded to prevent mechanical damage to lens 100.

According to the present invention, to fold lens 100 and insert it into loop 202 of apparatus 200, loop 202 is placed around protrusion 508 of disk 504 and lens 100 is placed onto surface 506 of disk 504. Using a forceps, lens 100 is forced into groove 502, whereby lens 100 becomes folded. Folded lens 100 is then forced along groove 502 with a forceps toward protrusion 508. Lens 100 is slid out of groove 502 into protrusion 508. With lens 100 extending partially out of protrusion 508, tail 204 of apparatus 200 is pulled to pull loop 202 off protrusion 508 and directly onto lens 100. Loop 202 holds lens 100 in the folded state. Folded lens 100 may then be inserted into eye 404 using the forceps while folded lens 100 is held within loop 202.

According to a preferred embodiment of the present invention, with lens 100 resting over groove 502 near protrusion 508 and loop 202 placed around protrusion 508, lens 100 may be grasped with a forceps from below, with the forceps inserted through protrusion 508. Lens 100 is then folded by pulling lens 100 into groove 502 with the forceps. Lens 100 is then pulled into protrusion 508 with the forceps, where loop 202 is slid off protrusion 508 onto lens 100. Folded lens 100 may then be directly inserted into eye 404. In this preferred embodiment, the entire procedure of folding lens 100, placing loop 202 over lens 100, and inserting lens 100 into eye 404 may be accomplished with one continuous grasp of lens 100 by the forceps, thereby reducing the risk of mechanical damage to lens 100.

Figure 8:
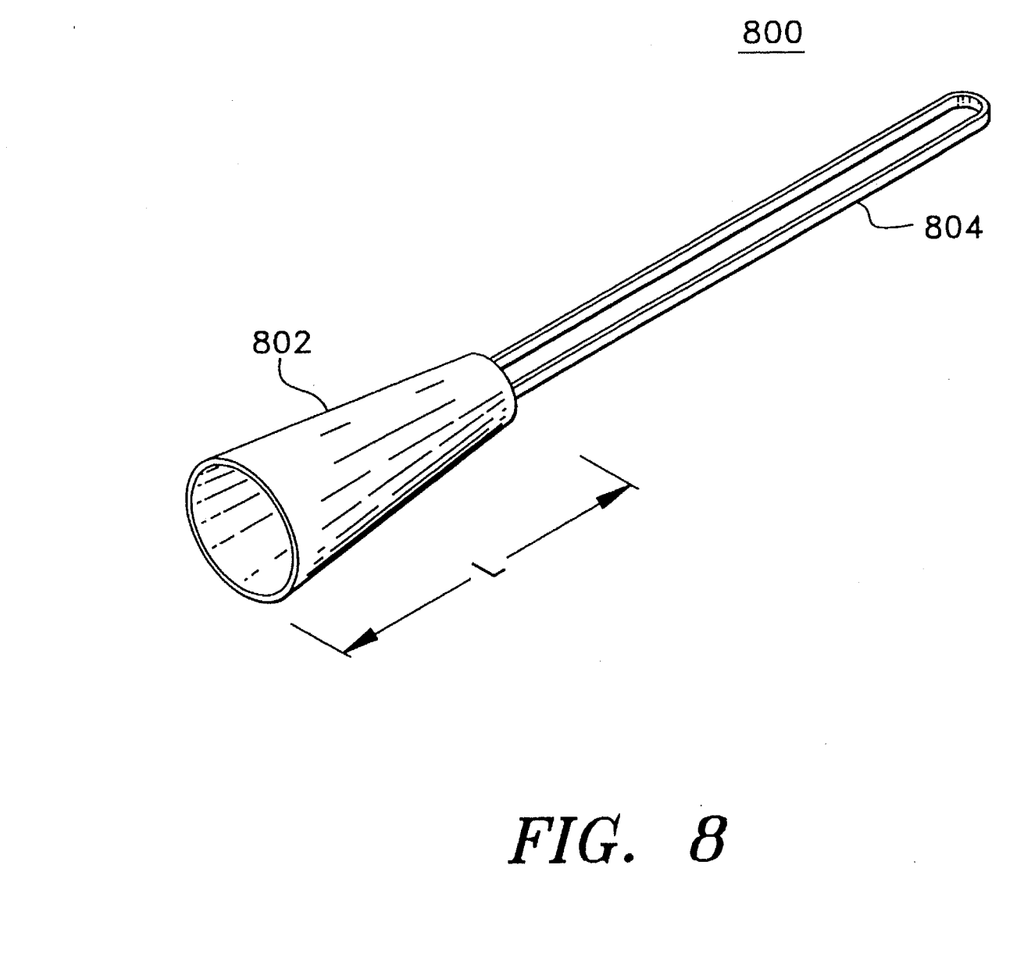
FIG. 8 shows a perspective view of an apparatus for inserting the lens of FIG. 1 into an eye, according to an alternative preferred embodiment of the present invention.

Referring now to FIG. 8, there is shown a perspective view of apparatus 800 for inserting an intraocular lens similar to lens 100 of FIG. 1 into an eye, according to an alternative preferred embodiment of the present invention. Apparatus 800 comprises loop 802 and tail 804. Loop 802 is hollow and open at both ends with the opening at one end larger than the opening at the other end. In a preferred embodiment, loop 80 is generally shaped like a frustum of a cone. The length L of loop 802 is preferably greater than the diameter of the large opening of loop 802 and preferably about the same length as the diameter of the intraocular lens to be inserted.

Tail 804 is attached to loop 802 at or near the small opening. In a preferred embodiment, both ends of tail 804 are attached to loop 802 at the small opening of loop 802.

Apparatus 800 is preferably made of a flexible sterilizable material such as a suitable clear plastic. Apparatus 800 may be made from a single piece of material or assembled from two or more pieces of similar or different material.

Figure 9:
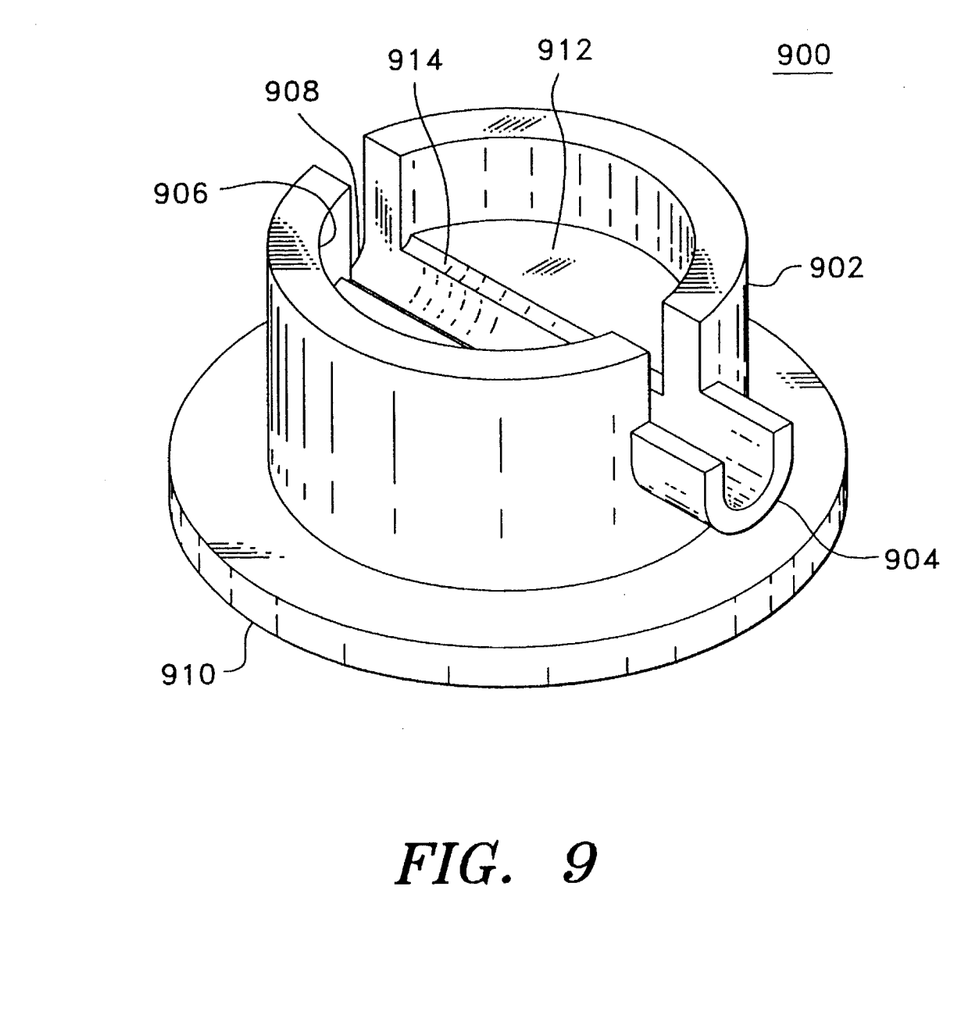
FIG. 9 shows a perspective view of an apparatus for folding the lens of FIG. 1 and inserting the folded lens into the apparatus of FIG. 8, according to an alternative preferred embodiment of the present invention.

Referring now to FIG. 9, there is shown a perspective view of apparatus 900 for folding an intraocular lens such as the lens of FIG. 1 and inserting the folded lens into apparatus 800 of FIG. 8, according to an alternative preferred embodiment of the present invention. Apparatus 900 comprises a base 910, a body 902, and a protrusion 904. In a preferred embodiment, base 910 and body 902 are both cylindrical with the diameter of base 910 larger than the diameter of body 902 and with body 902 attached at the center of the top surface of base 910.

Figure 10:
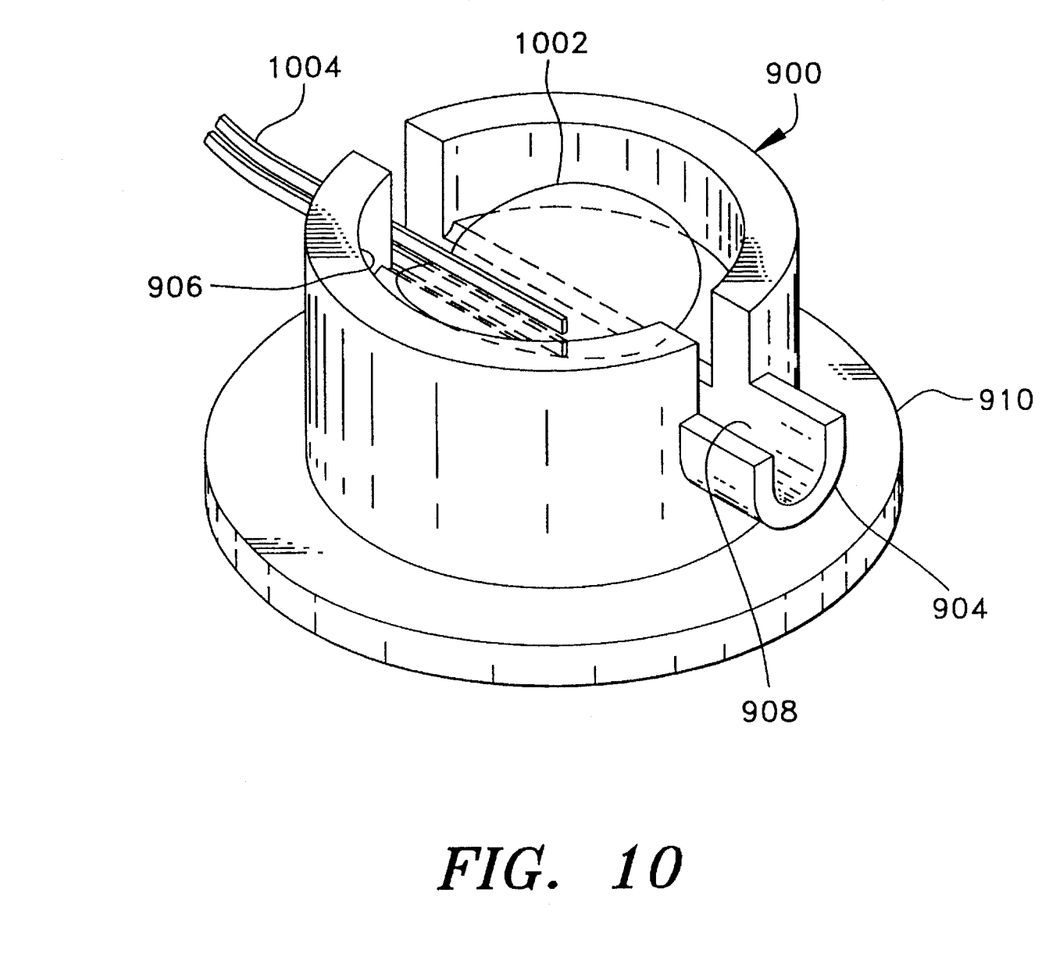
FIG. 10 shows a perspective view of the apparatus of FIG. 9 being used to fold an intraocular lens.
Figure 12:
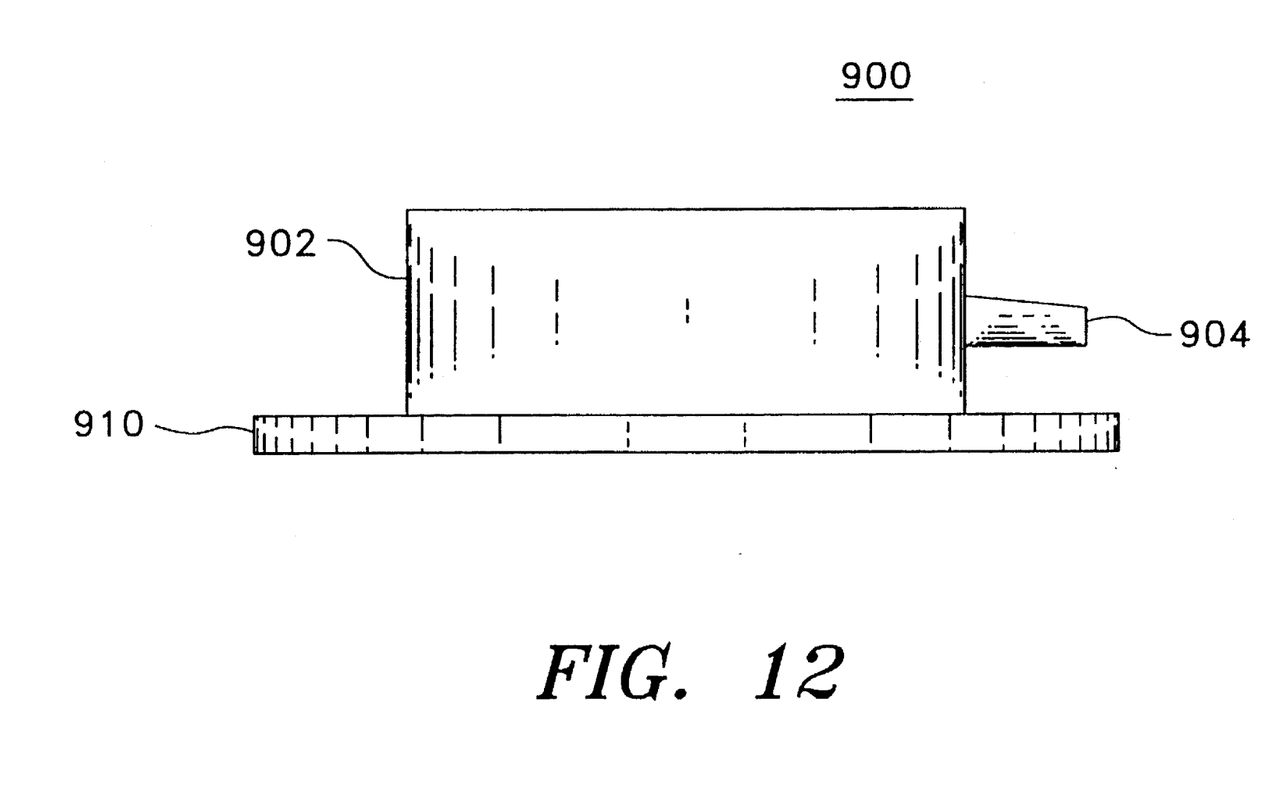
FIG. 12 shows a side view of the apparatus of FIG. 9.

Body 902 has a recess 906 (preferably cylindrical) in its top surface and a groove 908 running across the diameter of the recess 906 from one side of body 902 to the other. In a preferred embodiment, on each side of the groove 908, the surface of the recess 906 has a first surface 912 and a second surface 914, where the second surface 914 is immediately adjacent to the groove 908 and the second surface 914 is lower than the first surface 912. When an oblong intraocular lens is placed within the recess 906, the lower second surface 914 may be used to align the oblong lens with the groove 908 so that the lens will fold along its long axis when forced into the groove Referring also to FIG. 12, there is shown a side view of apparatus 900 of FIG. 9. In this preferred embodiment, protrusion 904 has a beveled profile with the smaller end of protrusion 904 further away from body 902 than the larger end. The beveled profile of protrusion 904 allows the frustum-shaped loop 802 of apparatus 800 to fit more snuggly over protrusion 904. As shown in FIG. 9, protrusion 904 is preferably and generally U-shaped with the upper side of protrusion 904 being open. Protrusion 904 is preferably aligned with groove 908 to form a contiguous groove across apparatus Referring now to FIG. 10, there is shown a perspective view of apparatus 900 of FIG. 9 being used to fold an intraocular lens 1002. Lens 1002 is placed within recess 906 and then forced into groove 908 using forceps 1004 or other instrumentality thereby folding lens 1002. Groove 908 is sufficiently deep such that lens 1002 folds in two when lens 1002 is forced into groove 908. Forceps 1004 may then be used to slide the folded lens 1002 toward protrusion 904. A purpose of base 910 is to provide the user with a surface of apparatus 900 to hold with one hand while manipulating the forceps 1004 with the other hand.

Figure 11:
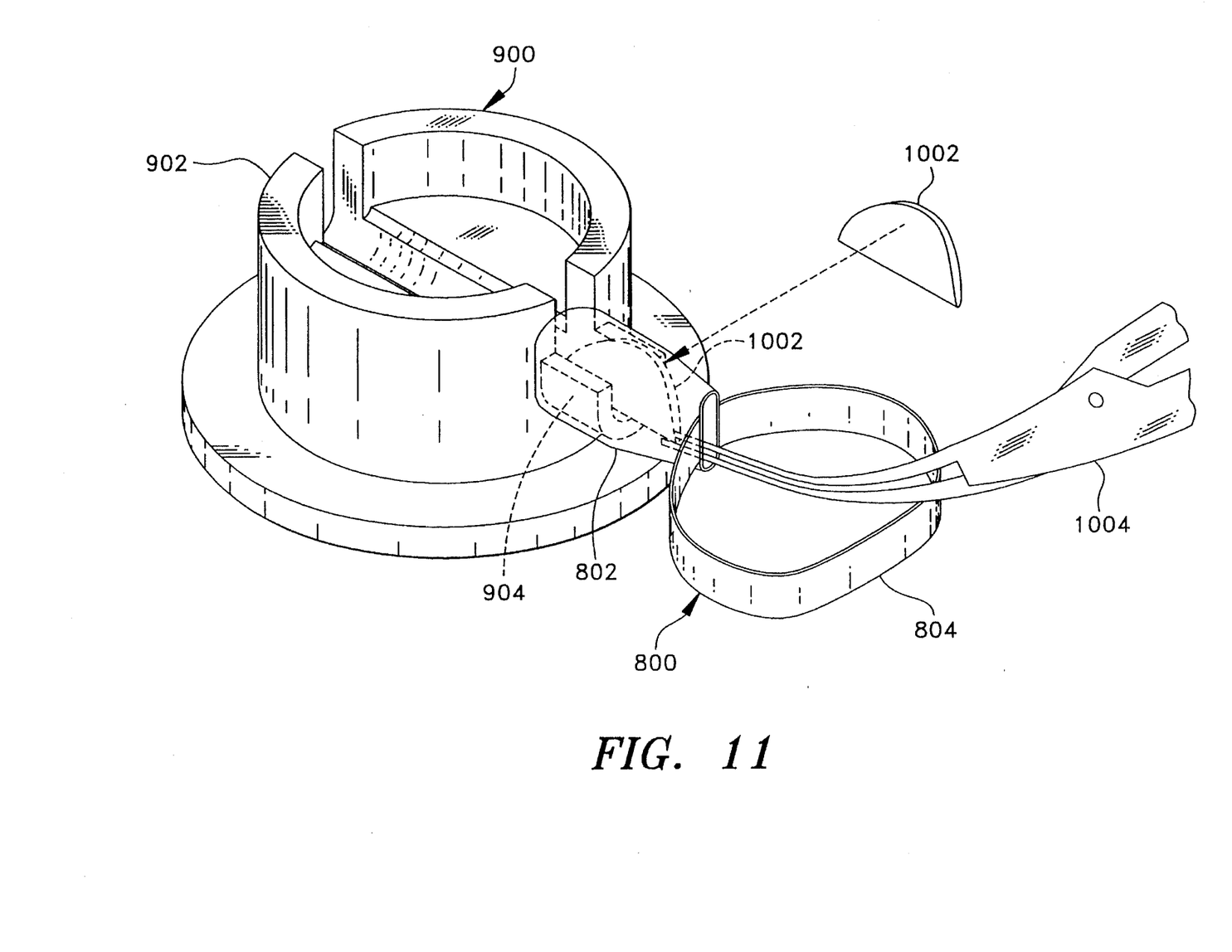
FIG. 11 shows a perspective view of the apparatus of FIG. 9 being used to insert a folded intraocular lens into the apparatus of FIG. 8.

Referring to FIG. 11, there is shown a perspective view of apparatus 900 of FIG. 9 being used to insert folded intraocular lens 1002 into apparatus 800 of FIG. 8. Loop 802 of apparatus 800 is placed over protrusion 904 of apparatus 900 with the large opening of loop 802 closest to body 902 and with tail 804 of apparatus 800 extending away from apparatus 900. With folded lens 1002 positioned within the groove of protrusion 904, folded lens 1002 is grasped with the forceps 1004 through the small opening of loop 802. When the folded lens 1002 is pulled away from apparatus 900 with the forceps 1004, loop 802 slides off protrusion 904 (because the folded lens 1002 preferably cannot pass through the small opening of loop 802) and over lens 1002 thereby retaining lens 1002 in a folded state.

Folded lens 1002 and loop 802 may then be inserted into an eye through an incision in a fashion similar to that depicted in FIG. 4 for apparatus 200. While continuing to grasp lens 1002 with forceps 1004 through the small opening of loop 802, tail 804 of apparatus 800 may be pulled to slide loop 802 intact off lens 1002 and onto the end of forceps 1004, thereby releasing lens 1002 and allowing it to unfold gently within the eye, where it may be positioned for proper placement. Apparatus 800 and forceps 1004 may then be removed from the eye through the incision at the same time.

Those skilled in the art will understand that apparatus 800 provides insertion of an intraocular lens through a relatively small incision. Apparatus 800 also permits relatively gentle release of the lens from its folded state. The ability to release the lens gently is an advantage over conventional devices for inserting intraocular lenses. These conventional devices discharge the lens within the eye with relatively great force, which may cause harm to the eye.

Another advantage of apparatus 800 with its frustum shaped loop 802 is its ability to be used with intraocular lenses of different types and sizes. For example, apparatus 800 may be used to insert intraocular lenses with or without haptics, as shown in FIG. 1, or intraocular lens that are either circular or oblong.

It will be understood that various changes in the details, materials, and arrangements of the parts which have been described and illustrated in order to explain the nature of this invention may be made by those skilled in the art without departing from the principle and scope of the invention as expressed in the following claims.

What is claimed is:

1. An apparatus for inserting a foldable intraocular lens into an eye, comprising:

(a) a loop, for maintaining the lens in a folded state, the loop having a large opening and a small opening and (b) a tail connected to the loop near the small opening, the loop being adapted to retain the lens in a folded position while the lens is grasped with a forceps and inserted into the eye through an incision in the eye; and the tail being adapted to be pulled to release the lens from the loop.

2. The apparatus of claim 1, wherein the loop is adapted to slide off the lens intact.

3. The apparatus of claim 1, wherein the loop has a shape of a frustum of a cone.

4. The apparatus of claim 1, wherein the tail is adapted to extend outside the eye through the incision.

5. The apparatus of claim 4, wherein the loop has a shape of a frustum of a cone and the tail is adapted to be pulled to release the lens from the loop while holding the lens with the forceps, thereby allowing the lens to unfold, wherein the loop is adapted to slide over the end of the forceps.

6. A method for inserting a foldable intraocular lens into an eye using a forceps, comprising the steps of:

(a) providing an apparatus having a loop and a tail, the loop having a large opening and a small opening;

(b) grasping the lens with the forceps, wherein the lens is held in a folded position within the loop of the apparatus;

(c) inserting the lens into the eye with the forceps through an incision in the eye; and (d) pulling the tail of the apparatus to release the lens from the loop of the apparatus.

7. The method of claim 6, wherein step (d) comprises the step of sliding the loop intact off the lens.

8. The method of claim 6, wherein step (c) comprises the step of inserting the lens into the eye, the tail of the apparatus extending outside the eye through the incision.

9. The method of claim 6, wherein step (d) comprises the step of pulling the tail of the apparatus to release the lens from the loop of the apparatus while holding the lens with the forceps, thereby allowing the lens to unfold, wherein the loop slides over the end of the forceps.

10. The method of claim 6, wherein step (b) further comprises the steps of:

(1) placing the lens on a disk having a groove on a surface of the disk and a protrusion at an edge of the disk, wherein the groove extends to the protrusion;

(2) placing the loop of the apparatus over the protrusion;

(3) folding the lens by forcing the lens into the groove;

(4) sliding the folded lens along the groove into the protrusion; and (5) slipping the loop off the protrusion and onto the folded lens.

11. The method of claim 10, wherein step (b)(5) comprises the steps of grasping the lens through the small opening in the loop and pulling the lens out of the protrusion whereby the loop slides off the protrusion and over the lens.

12. The method of claim 10, wherein step (b)(1) comprises the step of placing the lens on the disk, wherein:

the disk has a recess on a surface of the disk and the groove runs across the recess and the groove is aligned with the protrusion; and the protrusion is U-shaped for receiving a folded lens.

13. The method of claim 6, wherein step (a) comprises the step of providing the apparatus, wherein the length of the loop of the apparatus is greater than the diameter of the large opening of the loop.

14. The method of claim 6, wherein step (a) comprises the step of providing the apparatus, wherein two ends of the tail are attached near the small opening of the loop.

15. The method of claim 6, wherein step (a) comprises the step of providing the apparatus, wherein the loop has a shape of a frustum of a cone.

16. The method of claim 6, wherein step (a) comprises the step of providing the apparatus, wherein:

the loop has a shape of a frustum of a cone;

the length of the loop of the apparatus is greater than the diameter of the large opening of the loop;

both ends of the tail are attached to the small opening of the loop;

the tail of the apparatus extends outside the eye through the incision; and step (d) comprises the step of pulling the tail of the apparatus to release the lens from the loop of the apparatus while holding the lens with the forceps, thereby allowing the lens to unfold, wherein the loop slides off the lens intact and over the end of the forceps.

17. The method of claim 16, wherein step (b) further comprises the steps of:

(1) placing the lens on a disk, wherein the disk has a U-shaped protrusion at an edge of the disk, a recess on a surface of the disk, and a groove running across the recess and aligned with the protrusion;

(2) placing the loop of the apparatus over the protrusion;

(3) folding the lens by forcing the lens into the groove;

(4) sliding the folded lens along the groove into the protrusion;

(5) grasping the lens through an opening in the loop; and (6) pulling the lens out of the protrusion whereby the loop slides off the protrusion and over the lens.

18. An apparatus for folding a foldable intraocular lens and inserting the folded lens into a loop, comprising a disk having a U-shaped protrusion positioned at an edge of the disk, a recess on a surface of the disk, and a groove running across the recess and aligned with the protrusion.

19. The apparatus of claim 18, wherein the protrusion is beveled for receiving a loop having a large opening and a small opening.

20. The apparatus of claim 19, wherein the disk is cylindrical and attached to a base having a diameter larger than the diameter of the disk.

21. The apparatus of claim 18, wherein the disk is cylindrical and attached to a base having a diameter larger than the diameter of the disk.

22. A method for folding a foldable intraocular lens and inserting the folded lens into a loop, comprising the steps of:

(a) placing the lens on a disk having a U-shaped protrusion at an edge of the disk, a recess on a surface of the disk, and a groove running across the recess and aligned with the protrusion;

(b) placing the loop over the protrusion;

(c) folding the lens by forcing the lens into the groove;

(d) sliding the folded lens along the groove into the protrusion; and (e) slipping the loop off the protrusion and onto the folded lens.

23. The method of claim 22, wherein step (e) comprises the steps of:

(1) grasping the lens through an opening in the loop; and (2) pulling the lens out of the protrusion wherein the loop slides off the protrusion and over the lens.

* * * * *